US010206766B2

(12) United States Patent
Zachar et al.

(10) Patent No.: US 10,206,766 B2
(45) Date of Patent: Feb. 19, 2019

(54) TOOTHBRUSH SYSTEM FOR TREATING INTUBATED PATIENTS

(71) Applicant: Airway Medix S.A., Warsaw (PL)

(72) Inventors: Oron Zachar, Tel Aviv (IL); Yair Ramot, Kfar Maas (IL); Eizik Amar, Ashdod (IL)

(73) Assignee: Airway Medix S.A., Warsaw (PL)

( * ) Notice: Subject to any disclaimer, the term of this patent is extended or adjusted under 35 U.S.C. 154(b) by 0 days.

(21) Appl. No.: 15/668,726

(22) Filed: Aug. 4, 2017

(65) Prior Publication Data

US 2018/0078350 A1   Mar. 22, 2018

Related U.S. Application Data

(60) Provisional application No. 62/371,126, filed on Aug. 4, 2016.

(51) Int. Cl.
*A61C 17/22* (2006.01)
*A61C 17/02* (2006.01)
(Continued)

(52) U.S. Cl.
CPC .......... *A61C 17/221* (2013.01); *A46B 5/0095* (2013.01); *A46B 9/04* (2013.01);
(Continued)

(58) Field of Classification Search
CPC . A46B 13/02; A46B 15/0004; A46B 15/0053; A46B 5/0095; A46B 9/04;
(Continued)

(56) References Cited

U.S. PATENT DOCUMENTS

| 2,586,930 A | 2/1952 | Florence et al. |
| 4,466,150 A | 8/1984 | Jurt |

(Continued)

FOREIGN PATENT DOCUMENTS

| EP | 0992224 A2 | 4/2000 |
| EP | 1143876 A1 | 10/2001 |

(Continued)

OTHER PUBLICATIONS

JP2013-075033 Machine Translation (by EPO and Google) published on Apr. 25, 2013 Kawabata et al.
(Continued)

*Primary Examiner* — Marc Carlson
(74) *Attorney, Agent, or Firm* — Marc Van Dyke; Fourth Dimension IP

(57) ABSTRACT

An oral care system for a defined oral care cleaning cycle comprising a base module 100, a head module 150 comprising a toothbrush-bristle brush 165 disposed on a bristle-retaining surface of the head module, and a tail module 151. A multi-input/multi-display counter 149 is disposed on a base-module main body 110 of the main body 100. The multi-input/multi-display counter 149 independently displays first and second count-states, and includes first and second independently-operable user inputs that are respectively associated with the first and second count-states such that: (a) in response to user engagement of the first user input, the first count state is incremented or decremented; and (b) in response to user engagement of the second user input, the second count state is incremented or decremented.

4 Claims, 16 Drawing Sheets

(51) Int. Cl.
| | |
|---|---|
| *A61C 17/26* | (2006.01) |
| *A61C 17/34* | (2006.01) |
| *A46B 5/00* | (2006.01) |
| *A46B 9/04* | (2006.01) |
| *A61C 17/20* | (2006.01) |
| *A61C 17/36* | (2006.01) |
| *A46B 15/00* | (2006.01) |
| *A46B 13/02* | (2006.01) |

(52) U.S. Cl.
CPC .......... *A46B 9/045* (2013.01); *A46B 15/0053* (2013.01); *A61C 17/0202* (2013.01); *A61C 17/0208* (2013.01); *A61C 17/20* (2013.01); *A61C 17/225* (2013.01); *A61C 17/26* (2013.01); *A61C 17/34* (2013.01); *A61C 17/36* (2013.01); *A46B 13/02* (2013.01); *A46B 15/0004* (2013.01)

(58) Field of Classification Search
CPC . A46B 9/045; A61C 17/0202; A61C 17/0208; A61C 17/20; A61C 17/221; A61C 17/225; A61C 17/26; A61C 17/34; A61C 17/36
See application file for complete search history.

(56) References Cited

U.S. PATENT DOCUMENTS

| | | | |
|---|---|---|---|
| 5,456,361 A | 10/1995 | Walsh et al. | |
| 5,709,866 A | 1/1998 | Booras et al. | |
| 6,038,997 A | 3/2000 | Madden | |
| 6,129,547 A | 10/2000 | Cise et al. | |
| 6,186,782 B1* | 2/2001 | Luppi | A46B 11/0041 433/82 |
| 6,238,213 B1 | 5/2001 | Young et al. | |
| 6,241,412 B1 | 6/2001 | Spies et al. | |
| 6,622,333 B1 | 9/2003 | Rehkemper et al. | |
| 6,632,091 B1 | 10/2003 | Cise et al. | |
| 6,679,642 B1 | 1/2004 | Dillingham et al. | |
| 7,080,980 B2 | 7/2006 | Klupt | |
| 7,901,153 B1* | 3/2011 | Strider | A46B 5/0095 401/176 |
| 8,087,843 B2* | 1/2012 | Ottaviani | A46B 11/0041 15/22.1 |
| 8,302,776 B2 | 11/2012 | Lien | |
| 8,304,122 B2 | 11/2012 | Poshusta et al. | |
| 8,614,023 B2 | 12/2013 | Poshusta et al. | |
| 8,668,660 B2 | 3/2014 | Janssen et al. | |
| 9,027,192 B1* | 5/2015 | Cole | A46B 15/0004 15/105 |
| 9,144,298 B2 | 9/2015 | Fattori | |
| 9,343,758 B2 | 5/2016 | Poshusta et al. | |
| 2008/0166683 A1* | 7/2008 | Liao | A46B 15/00 433/80 |
| 2009/0197220 A1* | 8/2009 | Cindrich | A46B 5/0095 433/216 |
| 2009/0230050 A1 | 9/2009 | Jersey et al. | |
| 2010/0203399 A1 | 8/2010 | Poshusta et al. | |
| 2011/0070016 A1 | 3/2011 | Richardson | |
| 2011/0151404 A1* | 6/2011 | Dombrowski | A46B 15/00 433/96 |
| 2011/0214240 A1 | 9/2011 | Jimenez et al. | |
| 2013/0040216 A1 | 2/2013 | Poshusta et al. | |
| 2013/0149662 A1 | 6/2013 | Meloul-Tzubeli | |
| 2013/0298911 A1 | 11/2013 | Wlaschin et al. | |
| 2014/0106246 A1 | 4/2014 | Poshusta et al. | |
| 2015/0047134 A1* | 2/2015 | Prendergast | A61C 17/0208 15/4 |
| 2016/0113384 A1 | 4/2016 | Olson | |
| 2017/0071326 A1 | 3/2017 | Wu et al. | |
| 2017/0079419 A1 | 3/2017 | Wu et al. | |
| 2017/0215570 A1 | 8/2017 | Wu et al. | |
| 2017/0231379 A1* | 8/2017 | Wu | A46B 11/002 401/282 |
| 2017/0238688 A1 | 8/2017 | Wu et al. | |
| 2017/0258217 A1* | 9/2017 | Zachar | A61C 17/34 |
| 2017/0318946 A1 | 11/2017 | Davidson et al. | |
| 2018/0084898 A1 | 3/2018 | Vincent et al. | |
| 2018/0256430 A1* | 9/2018 | Zachar | A61G 15/16 |

FOREIGN PATENT DOCUMENTS

| | | |
|---|---|---|
| JP | 2013075033 A | 4/2013 |
| WO | WO2016185165 A1 | 11/2016 |
| WO | WO2017122200 A1 | 7/2017 |
| WO | WO2018060767 A1 | 4/2018 |

OTHER PUBLICATIONS

IS1.22 OralCare UK Issue3 Published Apr. 1, 2014.
Sage Product QCare Brochure Published Aug. 1, 2015.
International Search Report for PCT/IB2017/001354, dated Mar. 11, 2018.

* cited by examiner

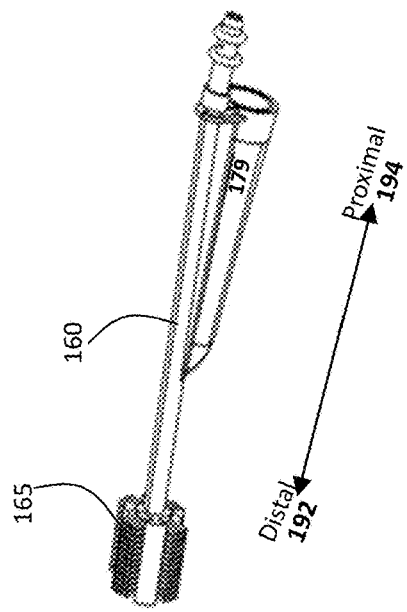
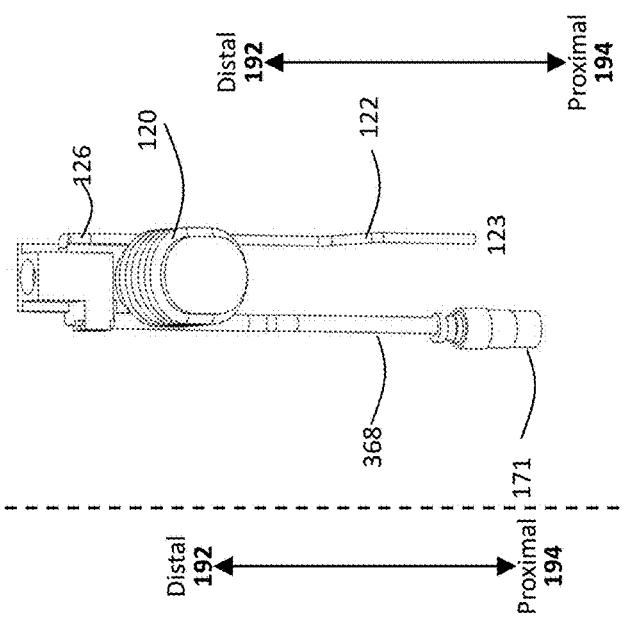
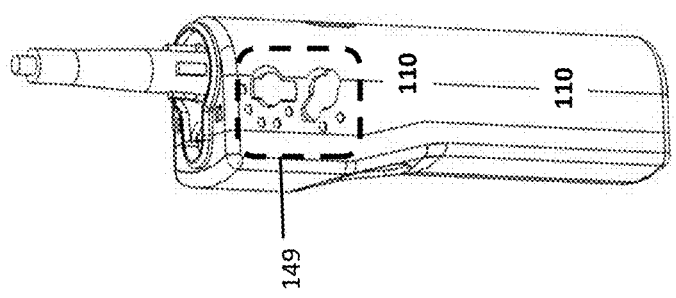
Fig. 2

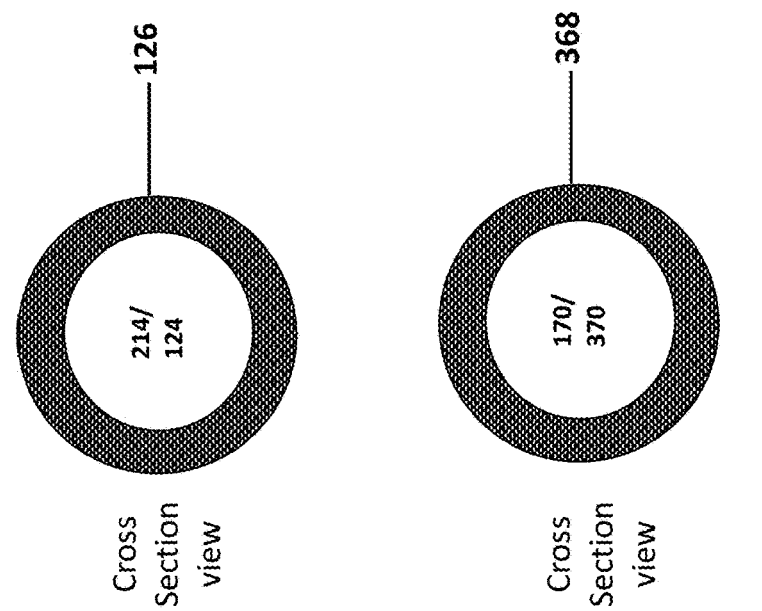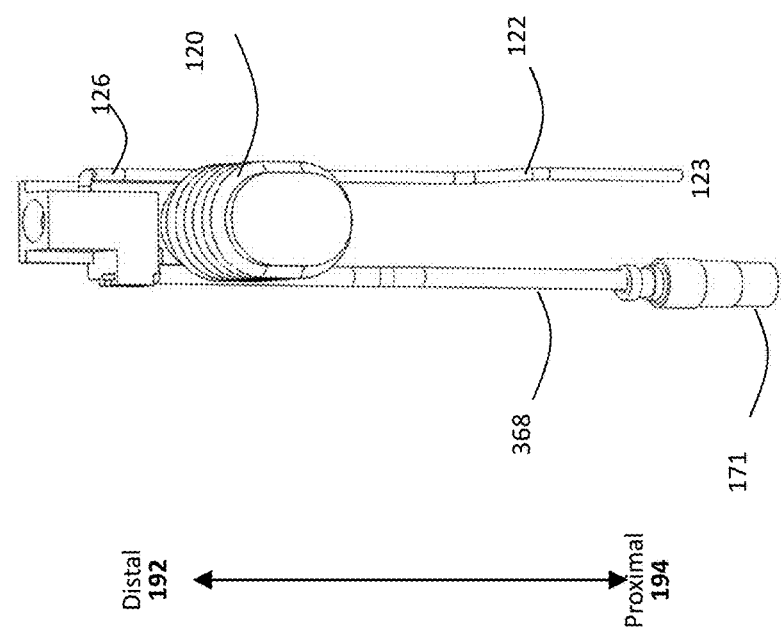
Fig. 6

TOOTHBRUSH SYSTEM FOR TREATING INTUBATED PATIENTS

FIELD OF THE INVENTION

The present invention relates to a multi-module system for brushing a subject's teeth, for example, as part of a multi-treatment oral care treatment cycle.

BACKGROUND

U.S. Pat. No. 7,866,477 discloses an oral care kit comprising a substantially rectangular box having oral care packs positioned therein. The oral care packs contain oral care devices useful for administering oral care treatment during a 24 hour oral care treatment cycle. The packs are useful for treating intubated patients in the hospital intensive care unit (ICU).

As shown in FIG. 1, the rectangular box comprises a plurality of partitions, each of which stores a different oral care pack. Not all of the packs stored in the partitions are identical. In one example, the number of toothbrush packs, catheter packs, suction swab packs with hydrogen peroxide, and suction swab packs with alcohol free mouthwash is 2:2:4:6, respectively.

The fact that each compartment may store a different type of oral care pack allows the user (e.g. a nurse in an ICU) to keep track of the different types of oral-care treatments, and in particular to apply the correct number of treatments in the correct ratio.

One feature of the oral care kit of U.S. Pat. No. 7,866,477 is the need to employ the internally portioned box. For example, the cost of packaging increases to the overall cost of the oral care. In addition, each box occupies space within the ICU, a location where space is at a premium. However, as noted above, the internally portioned box is indeed useful, as it allows a caregiver (e.g. ICU nurse) to easily track the number of each type of oral-care treatment previously applied to a patient, in order to apply the different types of oral-care treatments in the appropriate and pre-determined order. There is an ongoing need for systems and methods which facilitate oral care in the ICU at a reduced cost and/or in a manner that reduces the amount of space required in the ICU.

The following issued patents and patent publications provide potentially relevant background material, and are all incorporated by reference in their entirety: U.S. Pat. Nos. 6,186,782, 6,766,548, 6,920,659, 8,453,285 and 7,866,477. Any feature or combination of features disclosed in any of the aforementioned prior art documents may be combined with any feature disclosed herein.

SUMMARY OF EMBODIMENTS

Embodiments of the invention relate to a method, kit and apparatus for cleaning oral cavity and/or teeth of a subject, including but not limited to an intubated subject. The multi-module system comprises a head module, a tail module, and a base module, which are each directly or indirectly detachably attachable to each other. The head module comprises a toothbrush-bristle brush (i.e. a brush constructed of toothbrush bristles), the base module comprises a multi-input/multi-display counter and the tail module comprises a fluid container and at least two different lumen portions (i.e. suction-lumen portion and fluid-delivery lumen portion).

During operation, all three modules are attached (i.e. directly or indirectly attached) to each other to form a head-tail-base assembly. In particular, (i) the base module mechanically supports the head and/or the tail modules, and serves as a handle via which the user applies force to brush the subject's teeth using the head-module-disposed brush; (ii) fluid (e.g. cleaning fluid) is expelled from the tail-module-disposed fluid container, forced through a fluid lumen, and enters the subject's mouth (e.g. as a jet) via a fluid delivery lumen, e.g. disposed at or near the brush; and (iii) matter is suctioned out of the subject's mouth, where the suction is applied through a proximal suction port or connector (e.g. tapered connector) and communicated to a distal suction orifice via a suction lumen. The matter is suctioned out of the subject's mouth via the distal suction orifice.

Similar to the situation of U.S. Pat. No. 7,866,477, the subject (e.g. intubated patient in the ICU) may be subjected to a variety (e.g. at least two different types) of oral care treatments, one of which is the aforementioned toothbrushing treatment described in the previous paragraph. In addition, during his/her stay in the ICU, the same subject may also be subjected to other types of treatment, for example, a mouth-moisturizing treatment wherever a mouth moisturizer is applied to the gums—for example, the mouth-moisturizing treatment may be applied more frequently than the tooth-brushing treatments.

Over a period of several days, subjects/patients are commonly subjected to a repeated 24 hours cycle of oral cleaning. For reducing the risk of contamination, it is typical required that the brush-comprising components will be used only once and then disposed of. Prior art broke down the oral care kits into two type of components—single use heads and 24 h hours base handles. The 24 h cycle usage was recorded by the depletion of pre-ordered set packages.

In contrast, the present inventors recognize an advantage for breaking down the oral care kits into three types of components—short-use heads (e.g., single use), medium duration (e.g., 24 h) use tails, and extended-use (e.g., more than a week) base handles. The 24 h cycle recording is then maintained by counters disposed on the base, where the counters are to be reset to zero by the user after each 24 h day term.

As will be discussed below, the base module (which includes the multi-input/multi-display counter) is typically used for a longer period of time than either the head or tail modules. In one non-limiting example, the head module is single-use (e.g. per toothbrushing session), the base module is used for a much more extended period of time (e.g. per patient, for example, a week or more), and the tail module is used for an intermediate period of time (e.g. a new tail module is deployed to the base every 24 hours).

In one particular user-case a single base module remains bed-side for each patient during his/her entire stay in the ICU, and the multi-input/multi-display counter comprises two miniature (e.g. 2 cm×2 cm) electronic display-screens (e.g. liquid crystal display (LCD) screens) mounted side-by-side (i.e. next to each other) onto the base module (e.g. see, for example, FIG. 16 and the discussion at the end of the specification). Each display-screen is respectively associated with respective 'increment' button mounted immediately below the display screen. Thus, the multi-input/multi-display counter comprises two user inputs—the 'increment' button directly beneath the left display-screen is the first user input and the 'increment' button directly beneath the right display-screen is the second user input.

Upon start-up (i.e. power-on) each electronic display screen displays '0'—whenever the 'increment' button is pushed this increments the number displayed by the electronic display screen directly above the pushed 'increment' button (i.e. from 0 to 1 after a single depression of the increment button, from 1 to 2 the next time the increment button is pressed, and so one). At any given time, each electronic display screen displays a respective display integer displaying the number of times its respective/associated increment button was previously pushed. Thus, the multi-input/multi-display counter defines two 'count-states'—the integer displayed by the 'left' electronic display screen is the first count-state and the integer displayed by the 'right' electronic display screen is the second count-state.

Because the base module (i.e. on which the counter is disposed) remains bed-side during an entirety of the patient's stay in the ICU, the base module is a useful location for the multi-input/multi-display counter.

In particular, according to this use case, whenever the ICU patient is subjected to a first type of treatment (i.e. tooth brushing treatment), the care-giver manually engages the first user-input (i.e. by depressing the increment button beneath the left display screen)—this increments the first count-state (i.e. the integer on the left display screen—i.e. from 0 to 1, from 1 to 2, and so on). Whenever the ICU patient is subjected to a second type of treatment (e.g. mouth-moisturizing treatment), the care-giver manually engages the second user-input (i.e by depressing the increment button beneath the right display screen)—this increments the second count-state (i.e. the integer on the right display screen—i.e. from 0 to 1, from 1 to 2, and so on).

Each screen displays its respective display screen, which is visible to anyone who wishes to read the 'count-state' afterwards (e.g. the same nurse, or another nurse from the next shift).

In this manner, at any given time any nurse in the ICU may read from the base-module-disposed counter the number of previous treatments of the first and second types to which the intubated patient has previously been subjected. The nurse will read the base-mode and know the number of previous toothbrush-treatments and the number of previous mouth-moisturizing treatments—this will help the nurse decide if the next treatment to the intubated patient will be a toothbrush treatment or a mouth moisturizing treatment.

Since the base is re-used for different toothbrushing sessions and remains by the patient's bedside during an entirety of his/her stay in the ICU, this information (i.e. about the previous number of treatments of the first and second types) is readily available to any nurse in the ICU.

Since this information about the absolute and relative numbers of previous treatment of each type is readily available, there is no need to individually provide different types of oral care packs within compartments of a multi-compartment packaging, such as that disclosed in U.S. Pat. No. 7,866,477.

Thus, in some embodiments, the presently-disclosed teachings allow for the hospital to do away completely with per-patient oral-care kits of the type disclosed in U.S. Pat. No. 7,866,477. Instead, it is possible to employ a much more 'primitive' (but cheaper and less space-consuming) packaging where the oral care packs are stored in bins or bags—for example, bag or bin "A" includes only oral care packs of the first type, bag or bin "B" includes only oral care packs of the second type, and so on.

When a nurse approaches a given patient, s/he can check the base module disposed near the patient's bed to read, from the base-module-disposed counter, the number of previous treatments of each type applied to the patient. As such, the nurse can instantly ascertain the next type of oral-care treatment required in the oral care cleaning cycle, take the appropriate oral care element(s) (e.g. in a treatment pack) from the appropriate bag (e.g. bag or bin 'A' or bag or bin 'B'), and subjects the patient to this oral-care cleaning procedure using the oral care element(s) obtained from the appropriate bag. If appropriate (e.g. if the oral-care cleaning procedure involves brushing the patient's teeth), this oral care procedure may be performed using the base module as a toothbrush handle.

After performing a particular type of treatment, the nurse simply increments the counter appropriately. Thus, for treatments of type 'A' (e.g. using cleaning elements(s) from bag or bin 'A') the base-module-disposed multi-input/multi-display counter is operated to increment a first count-state (e.g. to depress the button directly beneath the left display screen to increment its display integer). For treatments of type 'B' (e.g. using cleaning elements(s) from bag or bin 'B') the base-module-disposed counter is operated to increment a second count-state (e.g. to depress the button directly beneath the left display screen to increment its display integer).

As noted above, the base module may be re-used many times, the base module (which includes the multi-input/multi-display counter) is typically used for a longer period of time than the tail module, which is used for a longer period of time than each head module (which is typically single-use). In different embodiments, a number of different geometric and/or mechanical features disclosed herein may facilitate appropriate module re-use—e.g. the tail module may be exposed to a lesser degree of contamination than the head module, and the base module may be exposed to a lesser degree of contamination than the tail module.

An oral care system for a defined oral care cleaning cycle is now disclosed. The oral case system includes: a. a base module 100 including a base-module main body 110 and a multi-input/multi-display counter disposed on the base-module main body; b. a head module 150 including a toothbrush-bristle brush 165 disposed on a bristle-retaining surface of the head module; c. a tail module 151 including: i. a fluid container 120, ii. a tail-module residing suction lumen portion 370. The oral care system also includes iii. a tail-module residing fluid delivery lumen portion 124 that is (a) separate from the suction tail-residing suction lumen portion, and (b) in fluid communication with the fluid container 120; where: the system includes attachment element(s) such that. The oral care system also includes a. the head and tail modules are detachably attachable to each other via the attaching element(s) to form a head-tail assembly where the head module is disposed distal to the tail module and where the toothbrush-bristle brush is disposed on a distal half of the head module. The oral care system also includes b. detachable attachment between the head 150, tail 151 and base 100 modules forms a head-tail-base assembly where the head module is disposed distal to both the tail module and the base module; the head-tail assembly includes: The oral care system also includes a suction lumen 270 including at least the tail-residing suction lumen portion 370, the suction lumen defining a distal suction-orifice 172 disposed in a distal half of head module or distal thereto, at least a majority of the head module being longitudinally spanned by the suction lumen, at least a majority of the tail module being longitudinally spanned by suction lumen. The oral care system also includes a fluid-delivery lumen 214 including at least the tail-residing fluid delivery lumen portion 124, the fluid delivery lumen defining a distal fluid-delivery orifice 218 disposed distally to the head module or in a longitudinal half thereof, the fluid delivery container in fluid communication with the distal fluid-delivery orifice 218 via an interior of the fluid-delivery lumen 214; and where: the multi-input/multi-display counter independently displays first and second count-states, and includes first and second independently-operable user inputs that are respectively associated with the first and second count-states such that: The oral care system also includes in response to user engagement of the first user input, the first count state is incremented or decremented. The oral care system also includes in response to user engagement of the second user input, the second count state is incremented or decremented.

Implementations may include one or more of the following features. The system where: i. a motor 116 resides on the base module; ii. the base-module-residing motor drives rotational and/or vibrational motion of the brush 165 when the system the head, tail and base modules are attached to each other to form the base-head-tail assembly. The system where: i. the motor 116 drives rotational motion of both a shaft 114 an eccentric weight 119 is mounted to the shaft 144, ii. the head assembly defines a proximal-facing cavity 177 into which the rotating eccentric weight is inserted. The system of any preceding claim where when the system the head, tail and base modules are attached to each other to form the base-head-tail assembly, plugging the suction lumen 170 lumen at both the proximal and distal ends thereof causes an interior of an entirety of the suction lumen 170 to be liquid-sealed away from the base module main body 100. The system of any preceding claim where an entirety of the suction lumen 170 between a distal orifice 172 thereof and a proximal connector 171 may be brought out of contact from the base module 110 while remaining whole and attached to brush 165 of the head module. The system of any preceding claim where a thickness ratio between a cross section of the suction distal-orifice and the fluid-delivery orifice is at least 1 or at least 1.25 or at least 1.5 or at least 1.75 or at least 2; The system of any preceding claim where a length ratio between respective lengths of the suction lumen 170 and fluid-delivery lumen 214 is at least 1.25 or at least 1.5 or at least 1.75 or at least 2 or at least 3 or at least 4 or at least 5. The system lacking a motor, where the brush 165 is operated only manually.

BRIEF DESCRIPTION OF THE DRAWINGS

FIG. 2 illustrates separate head, tail and base modules.

FIG. 6 illustrates a tail module.

DETAILED DESCRIPTION OF EMBODIMENTS

Embodiments of the present invention relate to systems, methods and kits for cleaning the oral cavity and/or teeth of a subject, including but not limited to an intubated subject.

The invention is herein described, by way of example only, with reference to the accompanying drawings. With specific reference now to the drawings in detail, it is stressed that the particulars shown are by way of example and for purposes of illustrative discussion of the preferred embodiments of the exemplary system only and are presented in the cause of providing what is believed to be a useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how several forms of the invention may be embodied in practice and how to make and use the embodiments.

For brevity, some explicit combinations of various features are not explicitly illustrated in the figures and/or described. It is now disclosed that any combination of the method or device features disclosed herein can be combined in any manner—including any combination of features—any combination of features can be included in any embodiment and/or omitted from any embodiments.

For the present disclosure, 'attachment' refers to direct or indirect attachment via attaching element(s) of the system or kit. When two modules are attached via an 'attachment element' the attachment element either be inherent to any of the modules (i.e. base, tail or head module) or could be an 'external element' that is external to the two modules and provided as part of a given system or kit. For example, the 'external element' may be part of a third module or may be any other external element. The external element may bridge between respective locations of each of the two attached modules. Examples of 'attachment elements' include but are not limited to fasteners, snaps, screw elements, spring-activated attachment elements, clamps, and magnetic attachment elements.

Figure 1:
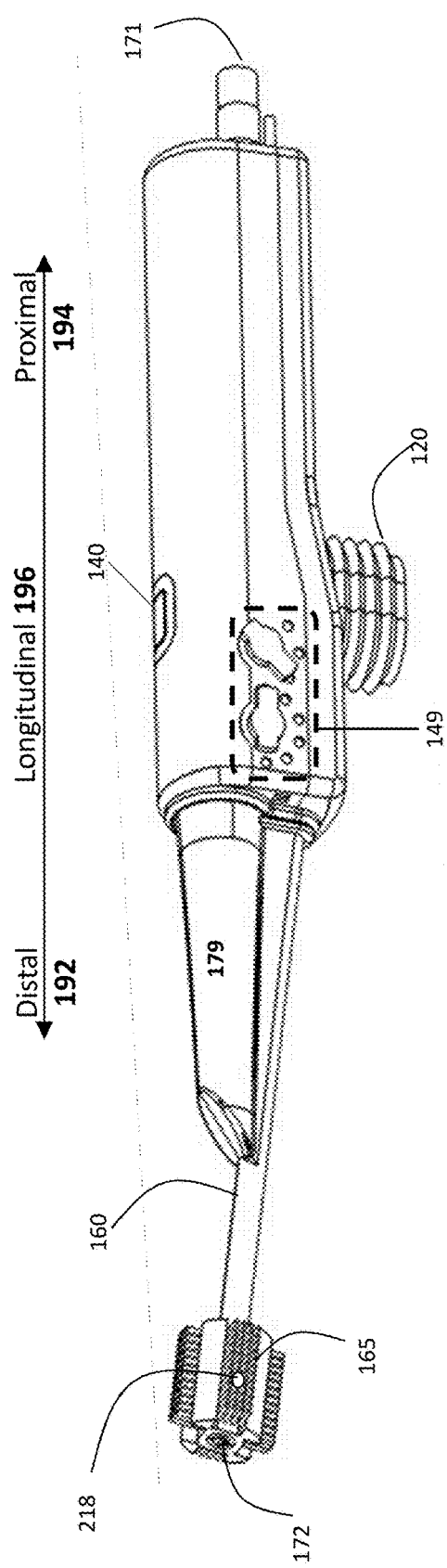
FIGS. 1, 3, 4, 8 and 9 illustrate a head-tail-base assembly of an oral care system.

For the present disclosure, when a first module is 'distal' to a second module, that means the first module as a whole may be considered 'distal' to the second module, even if portions of the 'first' module are proximal to portions of the second module. This is illustrated in FIGS. 1-2 where the head module 150 is 'distal' to both the base module 110 and the tail 151 module.

Modules
100—Base module
150—Head Module
151—Tail module
Elements of Multi-input/Multi-display Counter 149
145—first user-input (e.g. a first manually-rotatable pointer)
143—first counter-state visualization element (e.g. first plurality of ticks disposed around a rotation-center of the manually-rotatable pointer 145) for visualizing a first count-state (i.e. if there are N ticks there are N count-states defined by the combination of 145 and 143—the tick to which the rotatable-pointer 145 points to defines the first 'count-state')
146—second user-input (e.g. a second manually-rotatable pointer)
144—second counter-state visualization element (e.g. second plurality of ticks disposed around a rotation-center of the manually-rotatable pointer 146) for visualizing a second count-state (i.e. if there are N ticks there are N count-states defined by the combination of 146 and 144—the tick to which the rotatable-pointer 146 points to defines the second 'count-state')
Suction-related
170—suction lumen, at least a portion of which resides on the tail module 151
172—distal suction orifice of suction lumen 170

370—a tail-module residing suction lumen portion—i.e. portion of suction lumen 170 that resides in or on tail module 151
368—lumen-hosting body of tail-module residing suction lumen portion 370
470—a head-module residing suction lumen portion—i.e. portion of suction lumen 170 that resides in or on head module 150
171—proximal suction connector (e.g. tapered)—e.g. residing on tail module 151
138—suction switch
160—lumen-hosting body of head module (e.g. hosting 470 and/or 124)
380—proximal lumen-hosting body of tail module (e.g. proximal to container 120) (see FIG. 14)
Fluid-Delivery Related
214—fluid delivery lumen, at least a portion of which resides on the tail module 151
218—distal fluid delivery orifice of fluid-delivery lumen 214
120—tail-module-residing liquids reservoir/container
121—inlet/outlet hole of liquid reservoir/container
122—refill tube for refiling the reservoir/container (e.g. residing on the tail module 151)
123—input port for refill tube 121 (e.g. residing on the tail module 151)
124—a tail-module residing fluid delivery lumen portion—i.e. portion of fluid delivery lumen 214 that resides in or on tail module 151 (e.g. directly connected to outlet of 120)
126—lumen-hosting body of 124
160—lumen-hosting body of head module (e.g. hosting 470 and/or 124)
380—proximal lumen-husting body of tail module (e.g. proximal to container 120) (see FIG. 14)
Elements of Base Module
110—base main body
149—multi-input/multi-display counter disposed on base main body 110
156—handle portion of base main body 156
158—distal protrusion of base main body 156
Toothbrush-related Element (e.g. Power Brush)
165—toothbrush bristle brush disposed on the head module 150—a toothbrush bristle brush is a brush of toothbrush bristles. The toothbrush bristles of the brush are disposed on (and retained on) on a surface (e.g. of element 161) head module 150—this surface is referred to as a 'toothbrush-retaining' surface.
116—motor (e.g. base-module-residing)
179—sheath of head module 150
177—proximal-facing cavity of head module 160 (e.g. interior of sheath 179 into which distal portion 158 tip thereof)
114—base shaft-drive (e.g. residing on the base module 100)
119—Eccentric Rotating Mass
Axis/Direction
196—Longitudinal axis
194—proximal direction
192—distal direction Reference is made to FIG. 1 illustrates elements which illustrates an oral care system for brushing a patient's teeth and for monitoring different types of oral care operations. The oral care system is modular—in particular, is assembled from three modules: base module 100, head module 150, and tail module 151. FIG. 2 illustrates these individual modules.

As will be discussed below in greater detail, base module 100 includes (e.g. disposed on a main body of base module) a multi-input/multi-display counter 149 for tracking different types of oral care operations.

When used for toothbrushing, the oral care device of FIG. 1 is capable of simultaneously performing three operations—(i) a toothbrushing operating using toothbrush-bristle brush 165; (ii) a suction operation whereby matter (e.g. debris or biofilm) is suctioned into and through a suction lumen 170 (NOT SHOWN in FIG. 1) via suction orifice 172—towards this end, suction lumen 170 is attached to a source of negative pressure (NOT SHOWN) via a proximal end thereof (e.g. via suction connector 171 which is preferably tapered); and (iii) a fluid-delivery operation whereby fluid stored within container 120 is expelled therefrom, travels through fluid-delivery lumen 214 (NOT SHOWN in FIG. 1—see FIGS. 9, 5, 6 and 13-14) and exits therefrom via distal fluid delivery orifice 218.

In the example of FIG. 1, suction lumen 170 and fluid delivery lumen 218 are substantially not visible—however elements 171 and 172 (i.e. in fluid communication with each other via suction lumen 170) and elements 120 and 218 (i.e. an interior of 120 is in fluid communication with orifice 218 via fluid delivery lumen 214) are shown in FIG. 1. Also illustrated in FIG. 1 is lumen-hosting body 160 of head module 150—thus, in some embodiments (see cross section view of FIG. 5), at least a portion 470 of suction lumen 170 resides on or in head module 150—for example, in lumen-hosting body 160 of head module 150. Similarly, in some embodiments (see cross section view of FIG. 5), at least a portion 414 of fluid delivery lumen 214 resides on or in head module 150—for example, in lumen-hosting body 160 of head module 150. Also visible in FIG. 1 is sheath 179—this element may be used in embodiments where the toothbrush is a 'power brush' vibrations are transmitted from the base module 100 to the toothbrush 160 via a cavity (NOT SHOWN in FIG. 1—this is element 177) of sheath 179 which is part of head module 150.

Also illustrated in FIG. 1 is a longitudinal axis 196, a distal direction 192 and a proximal direction 194.

As shown in FIG. 2, is assembled from three modules, as opposed to many prior art devices assembled from only two modules. The modularity of the system is designed for the purpose of enabling three different life-time use (i.e., disposal action) of the elements, preferably in correlation with their contamination risk level. Thereby, the modularity of the system enables cost savings over the full system intended use cycle. Typically, for the present invention, head module(s) 150 is single-use since the toothbrush-bristle brush is directly exposed on its outer surface to contaminants within the patient's mouth. In contrast, tail module 151 may be used more than once, since the exposure is somewhat less and contaminated remains are mostly confined within internal lumens and not exposed on the surface. Base module 100 is used for the longest period of time—for example, during an entirety of a patient's stay (e.g. 3-15 days) within the ICU.

In addition, in the intensive care unit (ICU), multiple type of oral care operations are performed (e.g. by members of the nursing staff) on a single patient. In one example, a mouth moisturizing operation is performed relatively frequently (e.g. every few hours), while a tooth brushing operation is performed somewhat less frequently. During this time, the base module 100 would remain by the patient's bed.

As will be discussed below in greater detail, base module 100 includes (e.g. disposed on a main body of base module)

a multi-input/multi-display counter 149. In the non-limiting example of the figures (see FIGS. 1, 3, and 7), multi-input/multi-display counter 149 is mechanical (this is not a limitation) and comprises first and second user-input—in this non-limiting example, the inputs are first 145 and second 146 manually-rotatable pointers. In this example, the multi-input/multi-display counter 149 comprises first 143 and second 144 visualization elements—for example, first and second pluralies of ticks. The first plurality of ticks 143 is disposed around a center of rotation of the first 145 rotatable pointer. The second plurality of ticks 144 is disposed around a center of rotation of the second 146 rotatable pointer.

The multi-input/multi-display counter 149 independently displays first and second count-states. In the particular example of the drawings, the first count-state is the relative position of first rotatable pointer 145 relative to the first plurality of ticks 143, and the second count-state is the relative position of second rotatable pointer 146 relative to the second plurality of ticks 144.

Furthermore, multi-input/multi-display counter 149 includes first and second independently-operable user inputs (in this non-limiting example, the first 145 and second 146 rotatable pointer which rotate around different centers) that are respectively associated with the first and second count-states (in this example, the relative positions of the pointers with respect to the ticks respectively define).

Multi-input/multi-display counter 149 further provides the following feature—in response to user engagement (e.g. manual rotation of rotatable pointer 145 from one marker/tick to its neighbor)) of the first user input (i.e. the rotatable pointer 145), the first count state (e.g. the angular position of pointer 145 relative to its set of ticks 143) is incremented or decremented. For example, rotation in one direction to transition the pointer 145 orientation between neighboring ticks (e.g. from a first tick (i.e. of the set of ticks 143) to a neighboring tick that is to the right of the first tick) will serve to increment the count, and rotation in the opposite direction (i.e. counterclockwise) from a first tick to a neighboring tick that is to the will serve to decrement the count.

Multi-input/multi-display counter 149 further provides the following feature—in response to user engagement (e.g. rotation of pointer 146)) of the second user input (i.e. the rotatable pointer 146), the second count state (e.g. the position of pointer 146 relative to its set of ticks 144) is incremented or decremented. For example, rotation in one direction to transition the orientation of rotatable pointer 145 between neighboring ticks (e.g. from one tick of the second set of ticks 144 to a neighboring tick of the second set of ticks 144) will serve to increment the count, and rotation in the opposite direction will serve to decrement the count.

Figure 3:
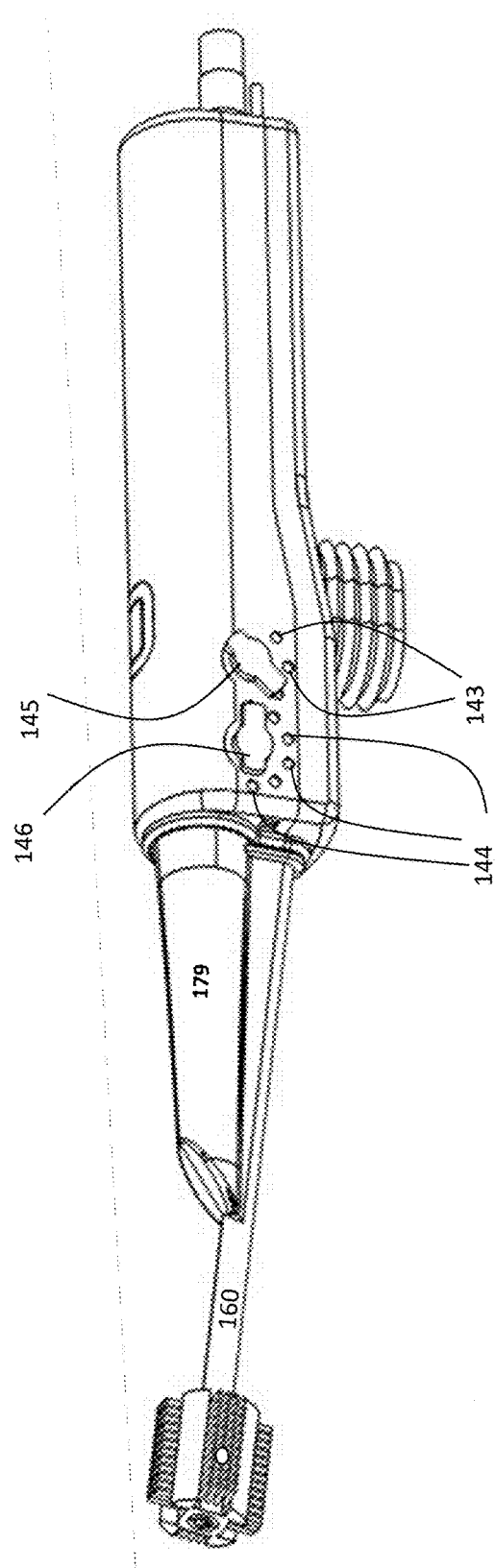

The term 'multi-input' means the counter 149 has two inputs—in the example of FIG. 3 pointer 145 is the first input and pointer 146 is the second input.

The term 'multi-display' means the counter is able to independently display (i) a first count-state (i.e. defined by the orientation of pointer 145 relative to the ticks 143—i.e. which specific and discrete tick (of the ticks 143) pointer 145 is pointing to) and (ii) and a second count-state (i.e. defined by the orientation of pointer 146 relative to the ticks 144—i.e. which specific and discrete tick (of the ticks 144) pointer 146 is pointing to.

Figure 15:
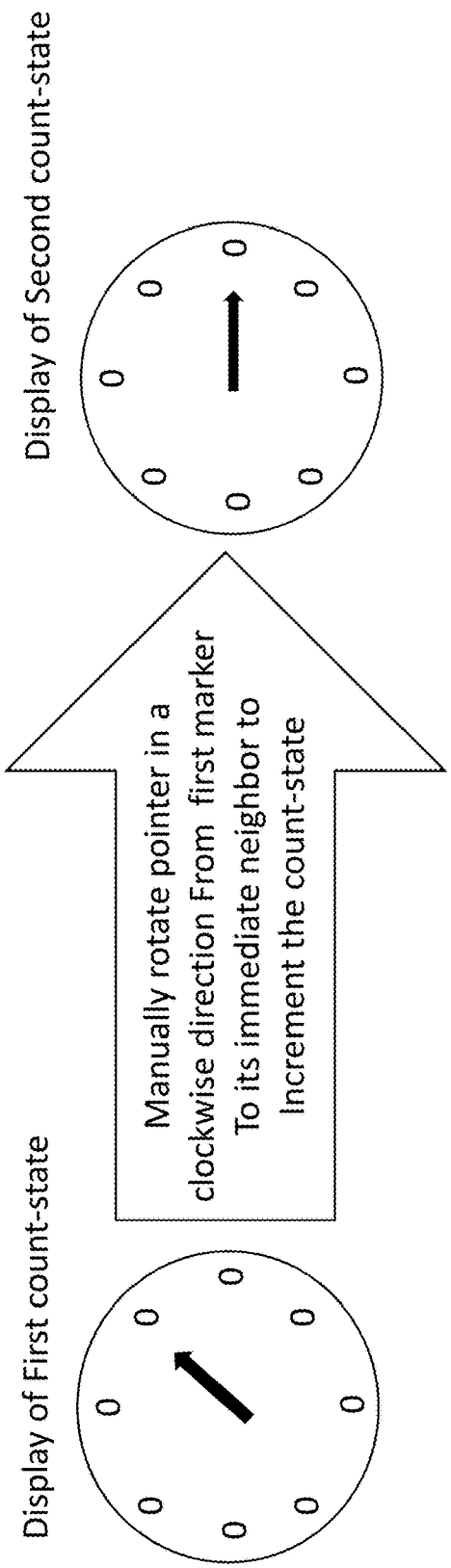
FIG. 15 illustrates one example of incrementing a count state.

One example of 'incrementing' a count state is shown in FIG. 15—in this example, the 'user input' is the single rotatable pointer which is engaged by manual rotation and responds to the manual rotation by moving from one tick to its neighbor, thereby incrementing the displayed count-state.

It will be appreciated that the manual multi-input/multi-display counter (i.e. comprising 143, 144, and 146) shown in FIG. 3 is just one example of manual counter—other manual or electrical/electronic counters may be employed. A non-limiting example of a different multi-input/multi-display counter 149 (e.g. electronic) is discussed below, with reference to FIG. 16.

Also shown in FIG. 1 is a mechanical switch 140—for example, the oral care device may include an electrical power brush, and switch 140 serves to turn on or off the brush. As will be discussed below, in some embodiments head module base module comprises a distal-protruding portion 158 of base module main body 110 (see FIG. 7) within which a rotating eccentric mass (see 119 of FIG. 9) causes vibrations which are transmitted to brush 165. For example, distal-producing portion 158 may be received into a proximal-facing cavity 177 of sheath element 179. Thus, sheath element 179 shown in FIG. 1 may be provided for power-brush embodiments. In other embodiments, the device functions as a 'manual toothbrush' with having no motor.

Figure 4:
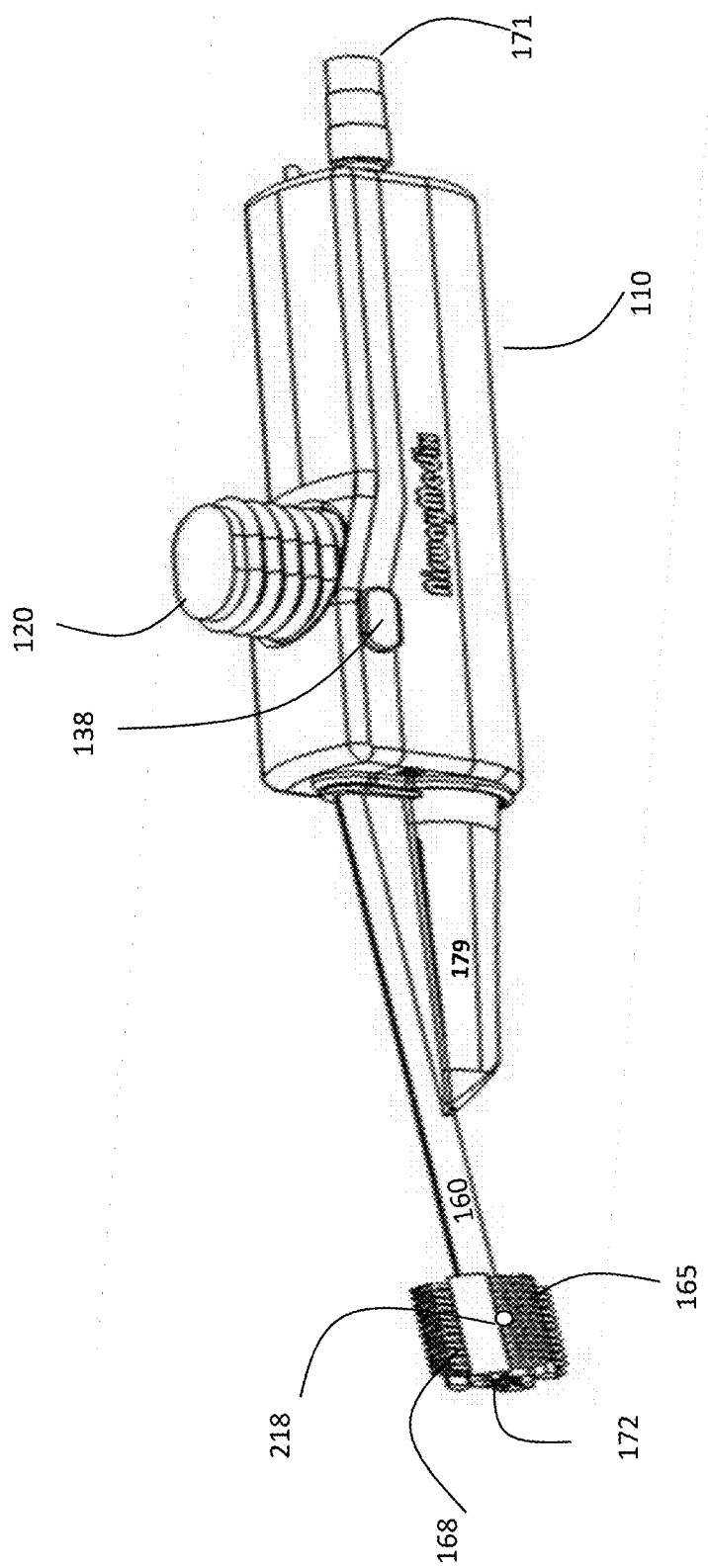

FIGS. 1 and 4 show all three (100, 150 and 151) modules of FIG. 2 assembled together to form a head-tail-base assembly. In the example of FIG. 1, fluid container faces down; in the example of FIG. 4, fluid container faces up. FIG. 4 shows suction switch 138 for turning on or shutting off suction—when suction is turned on negative pressure is conveyed from suction proximal connector 171 to suction orifice 172 via suction lumen 170 (NOT SHOWN in FIGS. 1 and 4).

Figure 5:
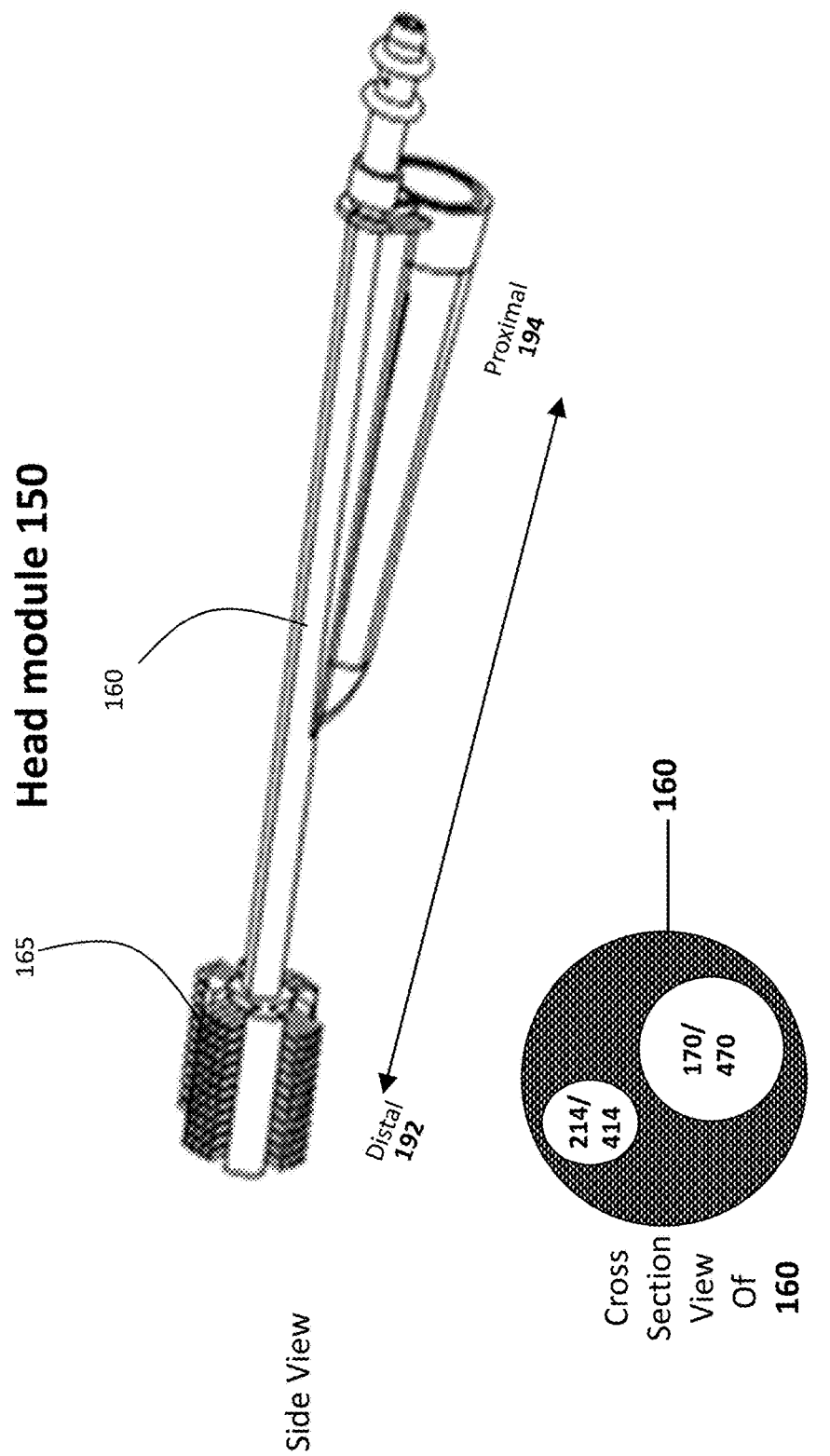
FIG. 5 illustrates a head module.
Figure 7:
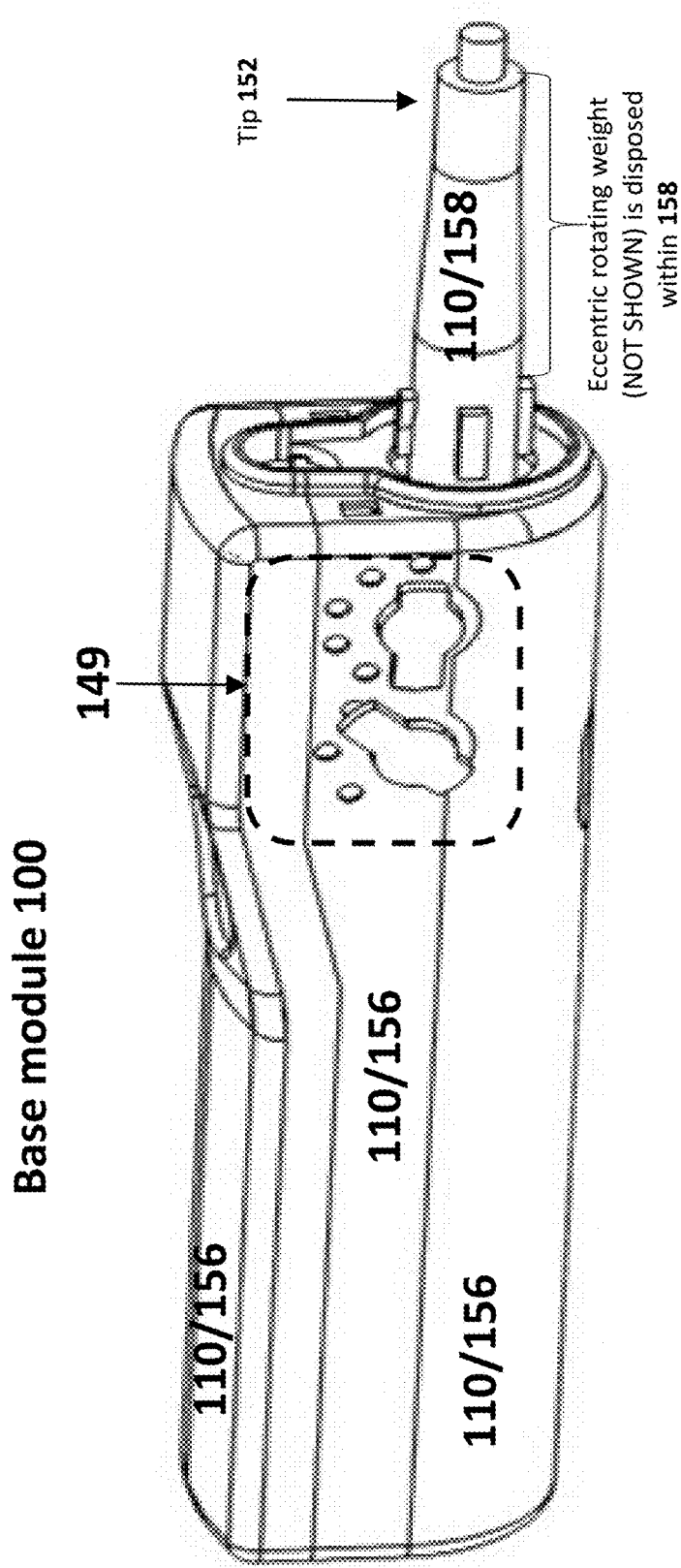
FIG. 7 illustrates a base module.

FIGS. 5-7 illustrate the three modules of FIG. 2.

FIG. 5 illustrates the head module 150 and includes a cross section of lumen-hosting body 160 of head module 150. In some embodiments (see also FIG. 13), lumen-hosting body 160 hosts a head-module residing portion 470 of suction lumen 170 and/or a head-module residing portion 414 of fluid-delivery lumen 214. As noted above, (i) 470 is part of suction lumen 170 that resides in the head module 150; and (ii) 414 is part of fluid delivery lumen 214 that resides in head module 150. In the cross-section view of 160 in FIG. 5, the notation '214/414' means that element 414 is at least a portion of fluid-delivery lumen 214. In the cross-section view of 160 in FIG. 5, the notation '170/470' means that element 470 is at least a portion of suction lumen 170.

Figure 13:
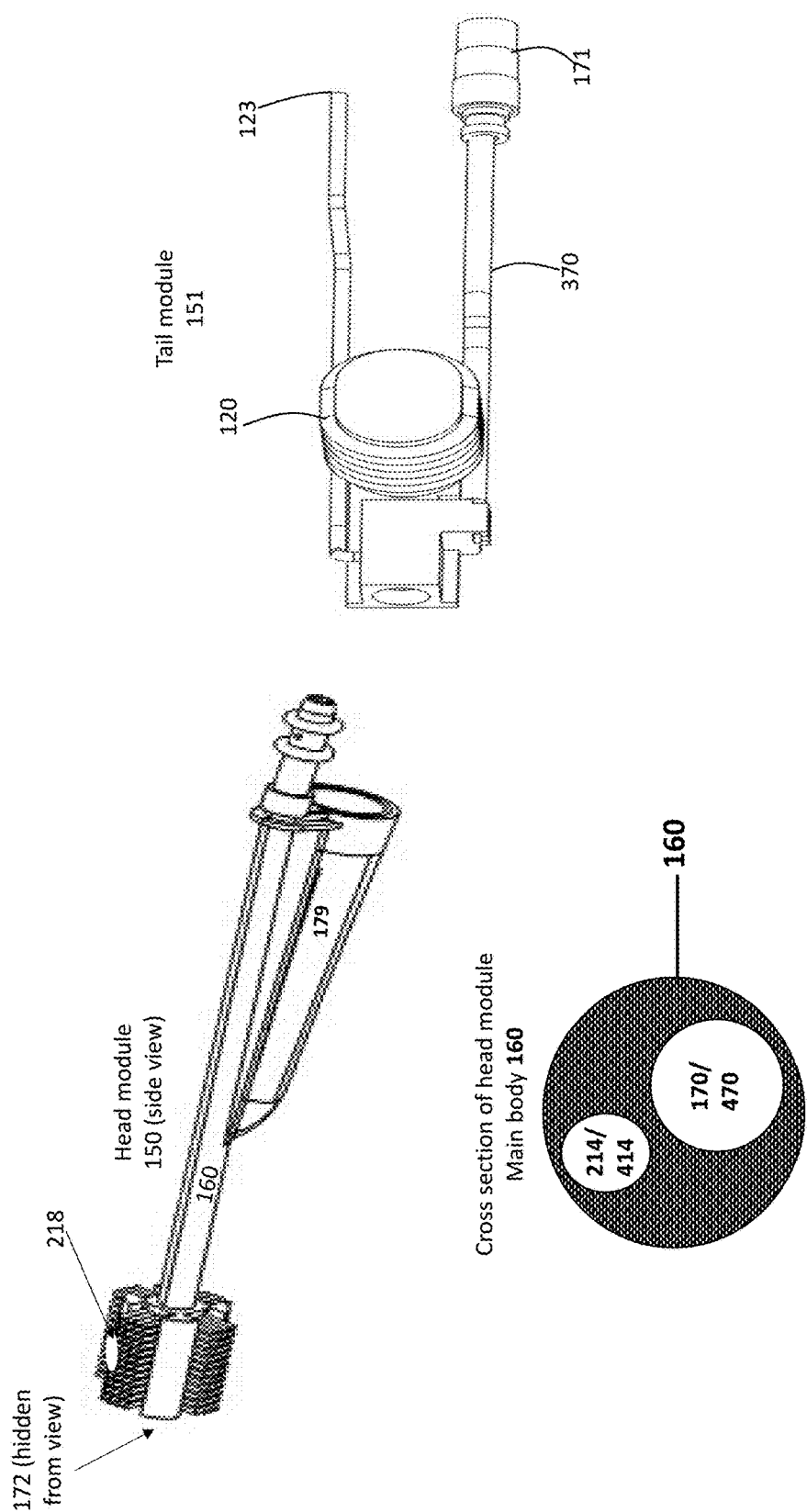
FIGS. 13-14 illustrate different lumen configurations.

In the example of FIGS. 5 and 13, at least a portion 414 of suction lumen 170 and at least a portion 414 of fluid delivery lumen 214 resides in head module 150. This is not a limitation—in the example of FIG. 14 the entity suction lumen 170 resides on tail module 151 and the entire fluid delivery lumen 218 resides on tail module 151.

Also shown in FIG. 5 is the distal 192 and proximal 194 directions—clearly, toothbrush-bristle brush 165 is disposed on a distal half of the head module 150.

FIG. 6 illustrates tail module 151 according to some embodiments of the invention. Illustrates in FIG. 6 is a tail-module residing portion 370 of suction lumen 170—e.g. the tail-module residing portion 370 is an interior of a tube, the exterior of which is labelled as 368. Element 368 is the lumen-hosting body of tail-module residing suction lumen portion 370—see the cross section on FIG. 6. In the cross-section view of 160 in FIG. 6, the notation '370/170' means that element 370 is at least a portion of suction lumen 170. In the cross-section view of 160 in FIG. 6, the notation '124/214' means that element 370 is at least a portion of fluid delivery lumen 214. Also illustrated in FIG. 6 is 126—lumen-hosting body of 124—together, elements 124 and 126 define a tube, the interior of which is 124. This tube (126+124) receives liquid (e.g. pressurized liquid) from an interior of container 120 via inlet/outlet hole 121 of liquid reservoir/container 120.

As shown in FIG. 6, the tail-module residing fluid delivery lumen portion 124 (within hosting body 126) is 'separate from the suction tail-residing suction lumen portion 370 (within hosting body 368)—they are not in fluid communication with each other. However, fluid delivery lumen portion 124 is in fluid communication with the fluid container 120—i.e. to receive fluid expelled from fluid container 120.

In some embodiments, tail module 151 includes a refill tube 122, and an end 123 refill tube 122 of which is illustrated in FIG. 6. During refill, liquid may enter from tube 122 into an interior of container 120 via inlet/outlet hole 121 of liquid reservoir/container 120.

As shown in FIG. 6, the tail-residing suction lumen portion 370 is relatively 'long' along the longitudinal direction 196—in this example, tail-residing suction lumen portion 370 clearly 'longitudinally spans' (i.e. along longitudinal direction 196) at least a majority of tail module 151. Because tail-residing suction lumen portion 370 is part of suction lumen 170, suction lumen 170 therefore necessarily 'longitudinally spans' (i.e. along longitudinal direction) at least a majority of tail module 151.

FIG. 7 illustrates base module 100 comprising base module main body 110 and multi-input/multi-display counter 149 disposed on base module main body 110. Multi-input/multi-display counter 149 was discussed above. Base module main body 110 may have any shape, and at least a portion thereof is typically used as a handle via which force is transmitted from the caregiver's hand to brush 165 to brush the patient's teeth. In the example of FIG. 7, base module main body 110 comprises a handle portion 156 which is typically held by the caregiver and a distally-protruding portion 158 which distally extends from the handle portion 156. Counter 149 may be disposed on handle portion 156 or on any portion.

For example, when the base module 100 and head module 150 are connected, distally-protruding portion 158 may extend into (and by inserted into) proximal-facing cavity 177 of head module 150 (e.g. proximal-facing cavity 177 within sheath). An eccentric mass 119 (see FIG. 9) within distally-protruding portion 158 is driven by motor 116 (see FIG. 9) to generate vibrations, which may be transmitted to head portion 150, in particular to brush 165 thereof. Insertion of distally-protruding portion 158 may extend into (and by inserted into) proximal-facing cavity 177 of head module 150 may serve to bring the rotating eccentric mass 119 closer to brush 165 to better transmit vibrations to brush 165.

Figure 8:
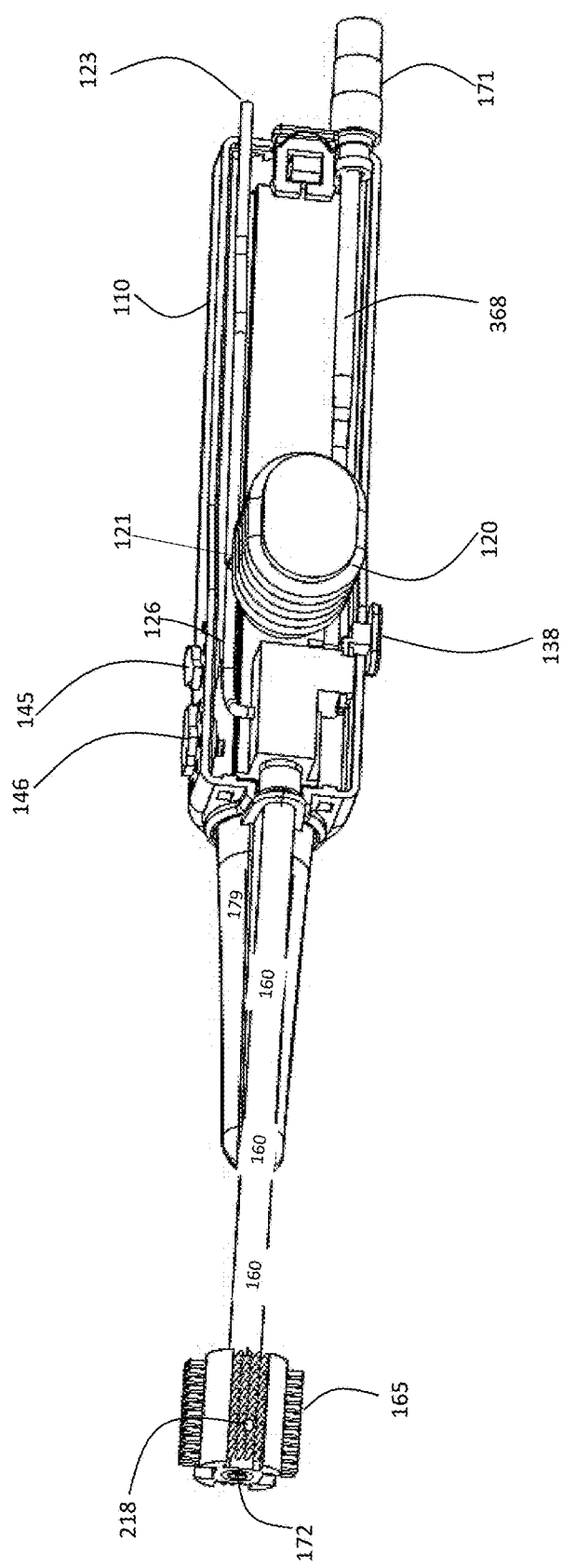

FIG. 8 is another view of base-head-tail assembly—i.e. all modules assembled together.

Figure 9:
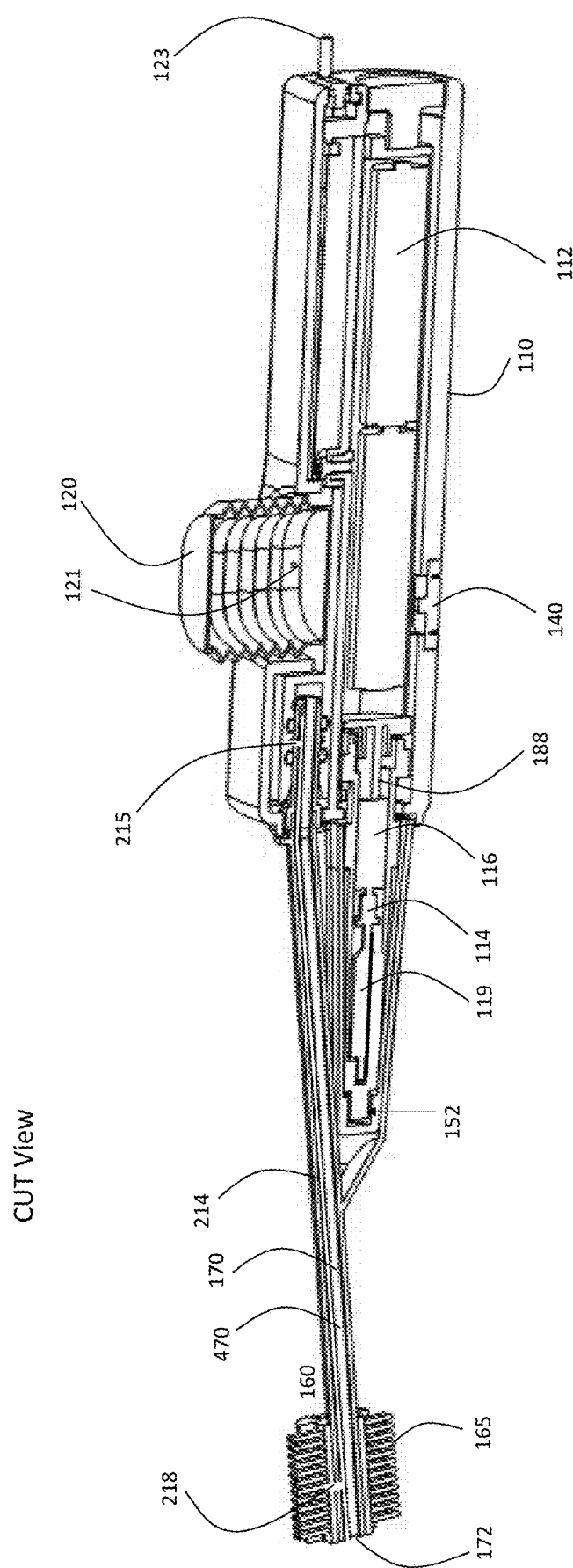

FIG. 9 is a cut view. FIG. 9 shows that motor 116 is supplied with electrical current from battery 112 via electrical line 188. Motor 116 drives rotation of shaft 114 to which eccentric weight 119 is mounted, thereby producing vibrations. Also illustrated in FIG. 9 is liquid outlet port 215 which via which fluid exits tube (124+126) en route to the head-module-residing portion 414 of fluid delivery lumen 214.

Figure 10:
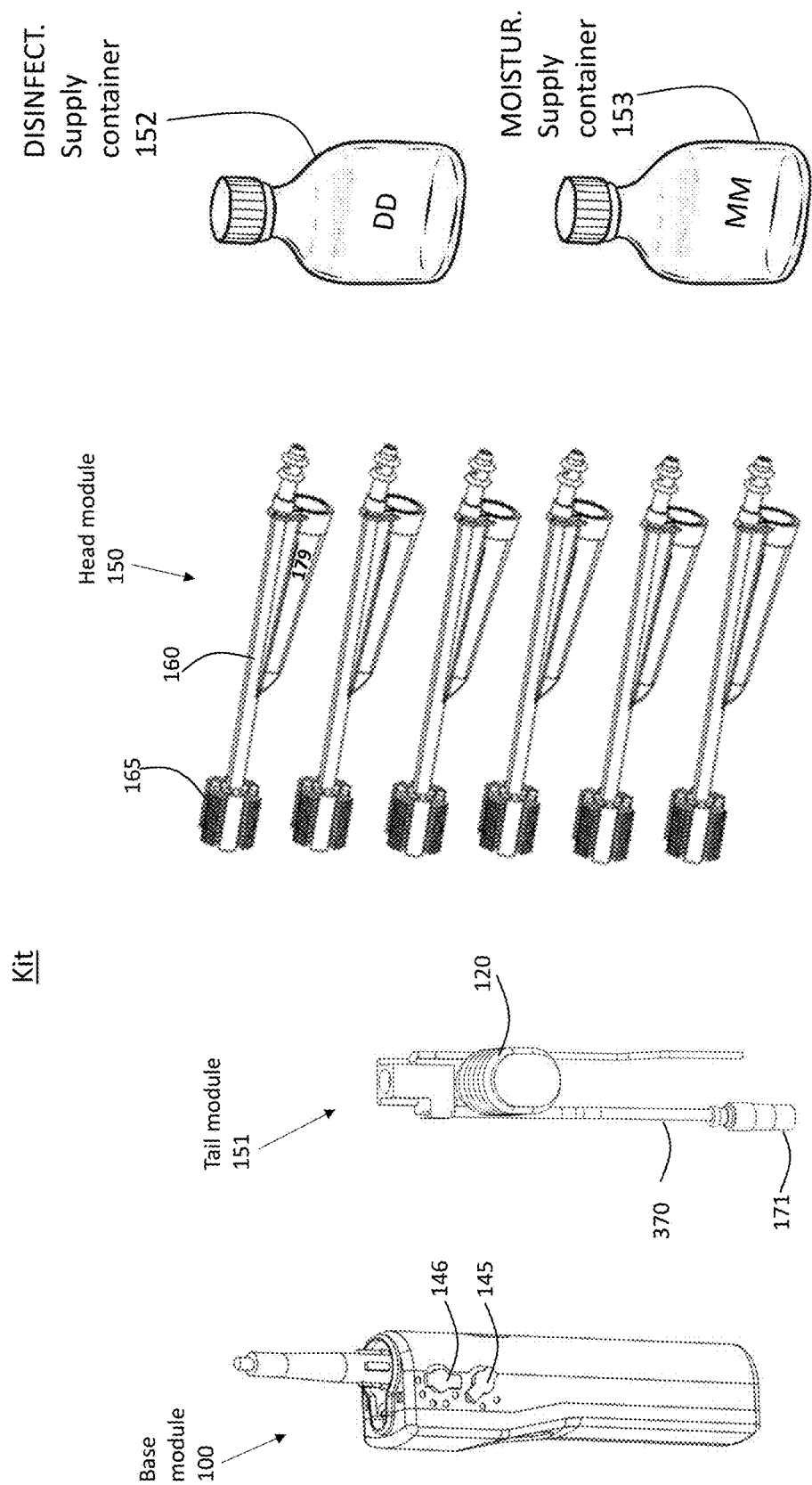
FIG. 10 illustrates a kit.

FIG. 10 illustrates a kit—for example, supply container 152 supplies liquid for brushing teeth using brush 165, and supply container 153 supplies liquid for mouth moisturizing operations which may or may not be performed using brush 165. Counter assembly 149 may be employed to keep track of these operations.

Figure 11:
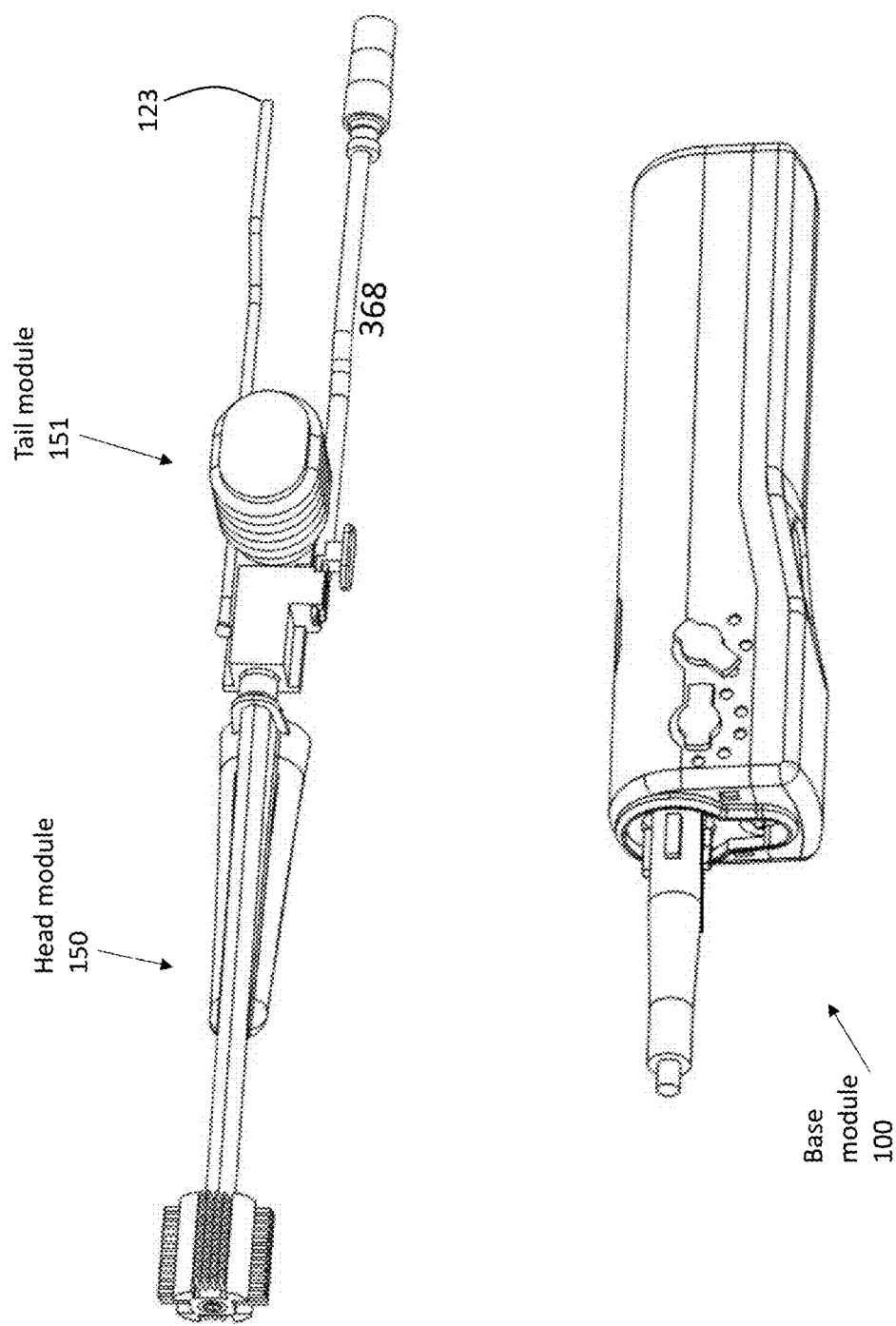
FIG. 11 illustrates a head-tail assembly of an oral care system.

FIG. 11 illustrates a configuration where head 150 and tail 151 modules are connected to each other, while both are disconnected from base 100.

Figure 12:
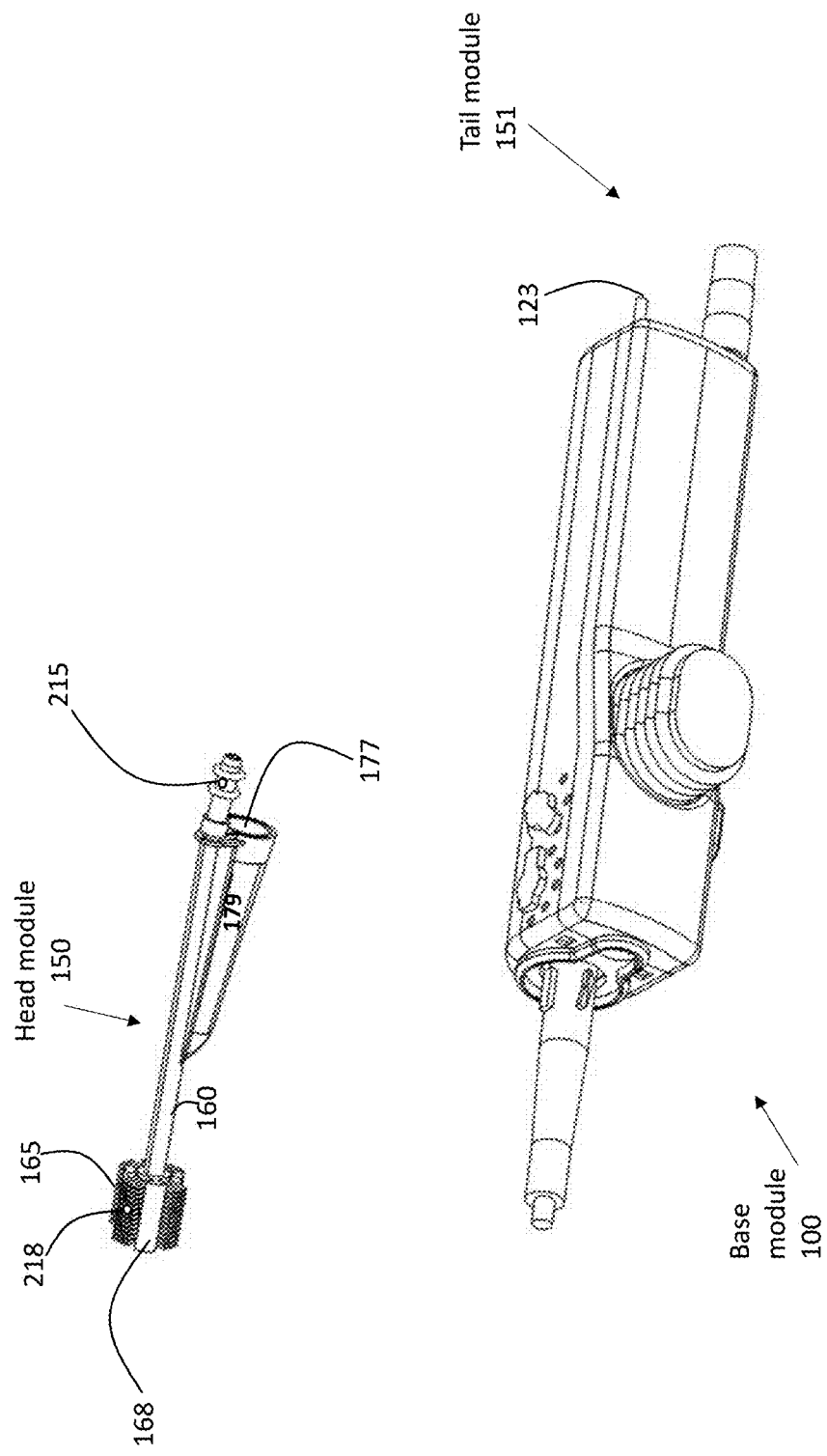
FIG. 12 illustrates a tail-base assembly of an oral care system.

FIG. 12 illustrates a configuration where base 100 and tail 151 modules are connected to each other, while both are disconnected from head module 150.

Figure 14:
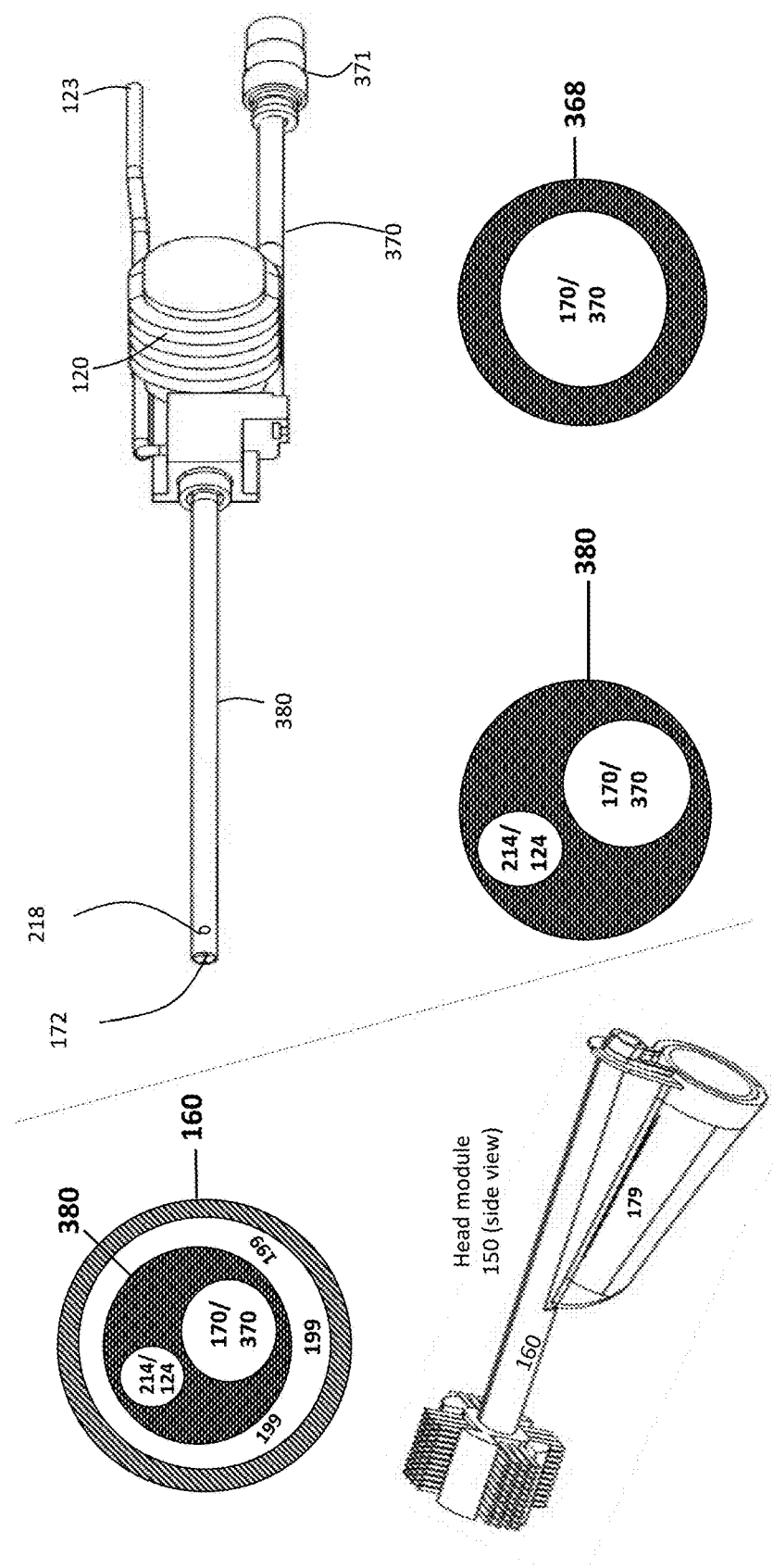

FIGS. 13 and 14 illustrate two different configurations. In the example of FIG. 13, (i) a first portion 414 of fluid delivery lumen 214 resides in the head module 150 and (ii) a second portion 124 of fluid delivery lumen 214 resides in the tail module 151. In the example of FIG. 13, (i) a first portion 470 of suction lumen 170 resides in the head module 150 and (ii) a second portion 370 of suction lumen 170 resides in the tail module 151.

In contrast, in the example of FIG. 14, an entirety of fluid delivery lumen 214 resides in the tail module 151 and an entirety of suction lumen 170 resides in the tail module 151. For the present disclosure, if a 'portion' (i.e. 124 or 370) of a lumen (i.e. suction 170 or fluid delivery 214) this means that the 'portion' (i.e. 124 or 370) may be (A) either less than an entirety of the lumen (i.e. suction 170 or fluid delivery 214) or (B) the 'portion (i.e. 124 or 370) is an entirety of the lumen (i.e. suction 170 or fluid delivery 214).

Thus, in the example of FIG. 14, proximal lumen-hosting body 380 of tail module 151 is such that body 380 is proximal to container 120. Within proximal lumen-hosting body 380 are tail-residing portions 124, 370 of fluid-delivery lumen 214 and suction lumen 170. As shown on the left side of FIG. 14 (cross section of element 160), proximal lumen-hosting body 380 is itself disposed in a lumen interior 199 of lumen-hosting body 160.

Within body 380, fluid delivery lumen portion 124 is parallel to (and next to) suction lumen portion 370—however, the interiors of the lumen are not in fluid communication with each other (i.e. separated by body 380)—thus, fluid delivery lumen portion 124 is still 'separate from' suction lumen portion 370.

As shown in both FIGS. 13 and 14, suction lumen 170 is present along at least a majority (e.g. at least 70% or at least 90% by length) of hosting element 160. In the example of FIG. 13 as element 470 (residing on the head module 150) and in the example of FIG. 14 as element 370 (residing on the tail module 151)—in both cases, within 160. This, and may be nature of the relationship between hosting element 160 and head module 150, it may be said (i.e. for both FIGS. 13 and 14) that suction lumen 170 longitudinally spans (i.e. along longitudinal direction 196) at least a majority of head module 150.

In the example of FIG. 13, both the suction orifice 172 (hidden from view in FIG. 13) and the distal fluid-delivery orifice 218 reside on the head module 150. In contrast, in the example of FIG. 14, both the suction orifice 172 (hidden from view in FIG. 13) and the distal fluid-delivery orifice 218 reside on the tail module 151. In both cases, when the had module 150 and tail modules 151 are attached to each other to form the head-tail assembly (i.e. either in the example of FIG. 11, or in the context of a head-tail-base assembly such as that illustrated in FIGS. 1, 3, 4, 8 and 9), it may be said that (i) distal suction-orifice 172 is disposed in a distal half of head module 150 (or distal thereto); and (ii) distal fluid-delivery orifice 218 is disposed distally to the head module 150 or in a longitudinal half thereof One salient feature provided by some embodiments of the invention relates to relative orientations of (i) an orientation vector of a plane of distal suction-orifice 172; (ii) an orientation vector of a plane of distal fluid-delivery orifice 218. In some embodiments, a plane of distal suction-orifice 172 and (ii) a plane of distal fluid-delivery orifice 218 are non-parallel so that an angle α therebetween is non-zero. In different embodiments, this angle α is at least 10 degrees or at least 20 degrees or at least 30 degrees. For the present disclosure, if this angle is defined as at least "X" degrees (where "X" is a positive number less than 90) this means that the angle α is between "X" degrees and 90 degrees.

Figure 16:
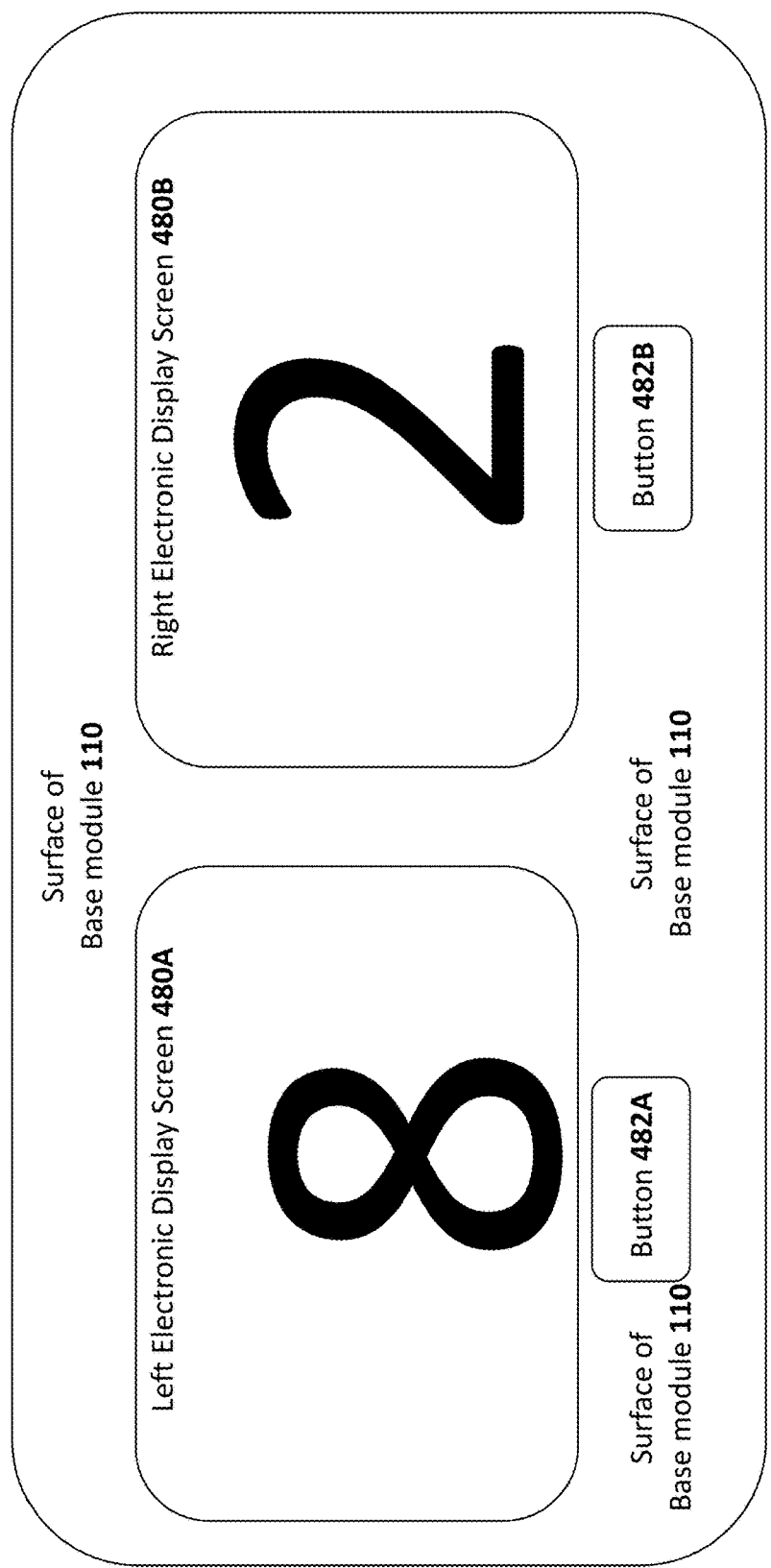
FIG. 16 illustrates one example of an electronic multi-input/multi-display counter.

A Discussion of FIG. 16

In the example of FIG. 3, a particular multi-input/multi-display counter 149 discussed. This multi-input/multi-display counter 149 comprises (i) a first rotatable pointer 145 (i.e. which functions as the 'first input' and is engaged by user manually rotating the pointer 145), (ii) a first plurality 143 of markers/ticks disposed around a rotation center of the first rotatable pointer 145 (i.e. pointer 145 and markers/ticks 143 collectively define and display the first count-state); (iii) a second rotatable pointer 146 (i.e. which functions as the 'second input' and is engaged by user manually rotating the pointer 146), (ii) a second plurality 144 of markers/ticks disposed around a rotation center of the second rotatable pointer 146 (i.e. pointer 146 and markers/ticks 144 collectively define and display the second count-state);

This is not a limitation. Another non-limiting example of a multi-input/multi-display counter 249 is now discussed.

This multi-input/multi-display counter 249 comprises two display-screens 480A, 480B mounted side-by-side (i.e. next to each other) onto a surface of the base module 110 and buttons 482A and 482B. Each display-screen 480 is respectively associated with respective 'increment' button 482 mounted immediately below the display screen—thus, button 482A is mounted below an electrically coupled to the left display screen 480A and button 482B is mounted below an electrically coupled to the right display screen 480B.

Thus, the multi-input/multi-display counter comprises two user inputs—the 'increment' button 482A directly beneath the left display-screen 480A is the first user input and the 'increment' button 482B directly beneath the right display-screen 482B is the second user input. Upon start-up (i.e. power-on) each electronic panel (480A or 480B) displays '0'—whenever the 'increment' button (button 482A for screen 480A or button 482B for screen 480B) is pushed this increments the number of the display screen directly above the 'increment' button (i.e. from 0 to 1 after a single depression of the increment button, from 1 to 2 the next time the increment button is pressed, and so one). At any given time, each display screen displays a respective display integer—thus, the multi-input/multi-display counter defines two 'count-states'—the integer displayed by the 'left' electronic panel and the integer displayed by the 'right' electronic panel.

In the example of FIG. 3, the 'user engagement' of the first input 145 was the user manually rotating pointer 145 from one tick (i.e. of 143) to its neighbor. In the example of FIG. 16, the 'user engagement' of the first input 482A is the user pressing button 482A—this increment the first count state (i.e. the number display on electronic display screen 480A). In the example of FIG. 3, the 'user engagement' of the second input 146 was the user manually rotating pointer 146 from one tick (i.e. of 144) to its neighbor. In the example of FIG. 16, the 'user engagement' of the second input 482B is the user pressing button 482B—this increment the second count state (i.e. the number display on electronic display screen 480B).

In FIG. 16 there are two count states—the '8' displayed by left screen 480A and the '2' displayed by the right screen 480B.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the present disclosure has been described with respect to various specific embodiments presented thereof for the sake of illustration only, such specifically disclosed embodiments should not be considered limiting. Many other alternatives, modifications and variations of such embodiments will occur to those skilled in the art based upon Applicant's disclosure herein. Accordingly, it is intended to embrace all such alternatives, modifications and variations and to be bound only by the spirit and scope of the appended claims and any change which come within their meaning and range of equivalency.

In the description and claims of the present disclosure, each of the verbs "comprise", "include" and "have", and conjugates thereof, are used to indicate that the object or objects of the verb are not necessarily a complete listing of features, members, steps, components, elements or parts of the subject or subjects of the verb.

As used herein, the singular form "a", "an" and "the" include plural references and mean "at least one" or "one or more" unless the context clearly dictates otherwise.

Unless otherwise stated, the use of the expression "and/or" between the last two members of a list of options for selection indicates that a selection of one or more of the listed options is appropriate and may be made.

Unless otherwise stated, adjectives such as "substantially" and "about" that modify a condition or relationship characteristic of a feature or features of an embodiment of the present technology, are to be understood to mean that the condition or characteristic is defined to within tolerances that are acceptable for operation of the embodiment for an application for which it is intended.

To the extent necessary to understand or complete the present disclosure, all publications, patents, and patent applications mentioned herein, including in particular the applications of the Applicant, are expressly incorporated by reference in their entirety by reference as is fully set forth herein.

What is claimed is:

1. An oral care system for a defined oral care cleaning cycle comprising:
   a. a base module 100 comprising a base-module main body 110 and a multi-input multi-display counter 149 disposed on the base-module main body;
   b. a head module 150 comprising a toothbrush-bristle brush 165 disposed on a bristle-retaining surface of the head module;
   c. a tail module 151 comprising:
      i. a fluid container 120,
      ii. a tail-module residing suction lumen portion 370;
      iii. a tail-module residing fluid delivery lumen portion 124 that is separate from the suction tail-residing suction lumen portion 370, and in fluid communication with the fluid container 120; wherein:
   the system includes attachment element(s) such that:

a. the head and tail modules are detachably attachable to each other via the attaching element(s) to form a head-tail assembly where the head module is disposed distal to the tail module and where the toothbrush-bristle brush is disposed on a distal half of the head module;

b. detachable attachment between the head 150, tail 151 and base 100 modules forms a head-tail-base assembly where the head module is disposed distal to both the tail module and the base module;

the head-tail assembly comprises:

a. a suction lumen 270 comprising at least the tail-residing suction lumen portion 370, the suction lumen defining a distal suction-orifice 172 disposed in a distal half of head module or distal thereto, at least a majority of the head module being longitudinally spanned by the suction lumen, at least a majority of the tail module being longitudinally spanned by suction lumen; and b. a fluid-delivery lumen 214 comprising at least the tail-residing fluid delivery lumen portion 124, the fluid delivery lumen defining a distal fluid-delivery orifice 218 disposed distally to the head module or in a longitudinal half thereof, the fluid delivery container in fluid communication with the distal fluid-delivery orifice 218 via an interior of the fluid-delivery lumen 214; and wherein:

the multi-input multi-display counter 149 independently displays first and second count-states, and includes first and second independently-operable user inputs that are respectively associated with the first and second count-states such that:

a. in response to user engagement of the first user input, the first count state is incremented or decremented; and b. in response to user engagement of the second user input, the second count state is incremented or decremented.

2. The system of claim 1 wherein:
i. a motor 116 resides on the base module;
ii. the motor drives rotational and/or vibrational motion of the toothbrush-bristle brush 165 when the head, tail and base modules are attached to each other to form the head-tail-base assembly.

3. The system of claim 2 wherein:
i. the motor 116 drives rotational motion of both a shaft 114 an eccentric weight 119 is mounted to the shaft 144;
ii. the head module defines a proximal-facing cavity 177 into which the rotating eccentric weight is inserted.

4. The system of claim 1, lacking a motor, where the toothbrush-bristle brush 165 is operated only manually.

* * * * *